United States Patent

Winter et al.

[11] Patent Number: 5,574,166
[45] Date of Patent: Nov. 12, 1996

[54] CRYSTALLINE FORM OF 2-(2-HYDROXY-3-α-CUMYL-5-TERT-OCTYLPHENYL)-2H-BENZOTRIAZOLE

[75] Inventors: Roland A. E. Winter, Armonk; Ramanathan Ravichandran, Nanuet; Mark S. Holt, West Nyack; Volker H. von Ahn, Mahopac; Joseph E. Babiarz, Amawalk, all of N.Y.; David G. Leppard, Marly, Switzerland

[73] Assignee: Ciba-Geigy Corporation, Tarrytown, N.Y.

[21] Appl. No.: 424,843

[22] Filed: Apr. 19, 1995

[51] Int. Cl.⁶ .................................. C07D 249/20
[52] U.S. Cl. .......................................... 548/260
[58] Field of Search ............................. 548/260

[56] References Cited

U.S. PATENT DOCUMENTS

| | | | |
|---|---|---|---|
| 4,278,589 | 7/1981 | Dexter et al. | 260/45.8 |
| 4,283,327 | 8/1981 | Dexter et al. | 260/45.8 |
| 4,587,346 | 5/1986 | Winter et al. | 548/260 |
| 4,675,352 | 6/1987 | Winter et al. | 524/91 |
| 4,973,701 | 11/1990 | Winter et al. | 548/260 |
| 5,073,448 | 12/1991 | Vieira et al. | 428/331 |
| 5,095,062 | 3/1992 | Winter et al. | 524/91 |
| 5,098,477 | 3/1992 | Vieira et al. | 106/22 |
| 5,240,975 | 8/1993 | Winter et al. | 524/91 |
| 5,364,749 | 11/1994 | Leppard et al. | 430/507 |

FOREIGN PATENT DOCUMENTS 49-67378  6/1974  Japan.

*Primary Examiner*—Patricia L. Morris
*Attorney, Agent, or Firm*—Luther A. R. Hall

[57] ABSTRACT

Soluble and thermally stable benzotriazole UV absorbers typified by those of formula I

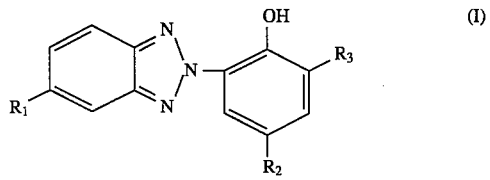

where $R_1$ is hydrogen or chloro, $R_2$ is alkyl or $-CH_2CH_2COOR_4$ where $R_4$ is hydrogen, alkyl or alkyl substituted with hydroxyl, and $R_3$ is α-cumyl, provide excellent light stability protection to electro coat, base coat or clear coat finishes. The new soluble, crystalline form of 2-(2-hydroxy-3-α-cumyl-5-tert-octylphenyl)-2H-benzotriazole is particularly effective.

5 Claims, No Drawings

CRYSTALLINE FORM OF 2-(2-HYDROXY-3-α-CUMYL-5-TERT-OCTYLPHENYL)-2H-BENZOTRIAZOLE

The instant invention pertains to polymer film coating compositions protected against catastrophic failure by the presence of soluble and thermally stable benzotriazole UV absorbers; and to a new soluble crystalline form of 2-(2-hydroxy-3-α-cumyl-5-tert-octylphenyl)-2H-benzotriazole which is particularly effective in such compositions.

BACKGROUND OF THE INVENTION

U.S. Pat. No. 4,278,589 describes the preparation of 2-(2-hydroxy-3-α-cumyl-5-tert-octylphenyl)-2H-benzotriazole and 2-(2-hydroxy-3-tert-octyl-5-α-cumylphenyl)-2H-benzotriazole. U.S. Pat. No. 4,278,589 also describes the preparation of 2-(2-hydroxy-3,5-di-α-cumylphenyl)-2H-benzotriazole. This latter compound is a very effective UV absorber, but unfortunately is relatively insoluble being soluble only at about the 14% (by weight) level in xylene. Since such aromatic solvents are threatened with banning because of environmental concerns, a diligent search for an effective benzotriazole which has the general light stabilizing effectiveness of 2-(2-hydroxy-3,5-di-α-cumylphenyl)-2H-benzotriazole and which is soluble in the new environmentally approved solvents is required. The several compounds mentioned earlier in this paragraph meet or essentially meet these new requirements.

Japanese Kokai 75/158588 describes the preparation of 2-(2-hydroxy-3-α-cumyl-5-methylphenyl)-2H-benzotriazole and 2-(2-hydroxy-3-methyl-5-α-cumylphenyl)-2H-benzotriazole as effective UV absorbers.

U.S. Pat. No. 4,283,327 discloses the preparation of 2-(2-hydroxy-3,5-di-tert-octylphenyl)-2H-benzotriazole and 5-chloro-2-(2-hydroxy-3,5-di-tert-octylphenyl)-2H-benzotriazole. U.S. Pat. Nos. 4,587,346; 4,675,352; 4,973,701; 5,095,062 and 5,240,975 describe the preparation of liquid benzotriazole mixtures by the post alkylation of preformed benzotriazoles using higher alkenes and an acid catalyst. Such products are complex liquid mixtures of various related benzotriazoles and are soluble in the environmentally acceptable solvents. However, while these UV absorbers are quite soluble in environmentally acceptable solvents, they do not have the thermal stability of the benzotriazole compounds which are substituted in the 3-position by an α-cumyl moiety.

The instant benzotriazole compounds are substituted in the 3-position with a α-cumyl group and in the 5-position usually with either a mixture with various alkylated moieties as substituents or are single compounds substituted with one bulky, tert-alkyl group. These materials are more soluble in common coatings solvents than the tris-aryl-s-triazines that are functionalized with simple alkyl groups. Common coatings solvents include xylene, methyl amyl ketone, butyl cellosolve, butyl carbitol and methyl isobutyl ketone. This functionality in combination with the high molecular weight of the compounds provides the instant compounds with a low migratory propensity when incorporated into the base coat of a clear coat/base coat system.

OBJECTS OF THE INVENTION

The object of this invention is to provide a method for protecting an electro coat/base coat/clear coat coating system against delamination from a substrate by incorporating therein a selected soluble and thermally stable benzotriazole.

Another object of this invention is to provide a new soluble crystalline form of 2-(2-hydroxy-3-α-cumyl-5-tert-octylphenyl)-2H-benzotriazole.

Still another object of this invention is to provide organic or photographic compositions stabilized against the deleterious effects of actinic light using the new soluble benzotriazoles substituted in the 3-position of the phenyl ring by an α-cumyl moiety.

DETAILED DISCLOSURE

The instant invention pertains to a new soluble crystalline form of 2-(2-hydroxy-3-α-cumyl-5-tert-octylphenyl)-2H-benzotriazole, that is a compound of formula I

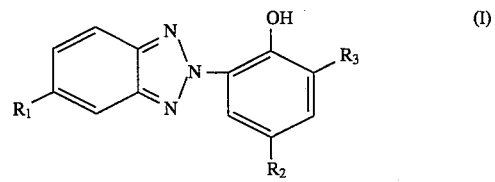

wherein $R_1$ is hydrogen, $R_2$ is tert-octyl and $R_3$ is α-cumyl.

This compound of formula I is useful as a stabilizer for organic polymers as taught in U.S. Pat. No. 4,278,589. This compound of formula I is disclosed in said patent in Example 18 as being an off-white powder melting at 88°–90° C. As such, the powdery product has defects in terms of handling and apparent density, exhibiting poor flowability, meterability and storage stability.

It has now been found that the compound of formula I can be obtained in a different crystalline modification as purified crystalline particles which exhibit acceptable properties in respect to handling, apparent density, flowability, meterability and storage stability.

The new modification is characterized by a novel crystalline form as off-white crystals melting in the range of 109°–111° C.; and by an X-ray diffraction pattern obtained using Cu—Kα which exhibits diffraction angles (2Θ) as seen below:

| Peak No. | Diffraction Angle |
|---|---|
| 1 | 9.6 |
| 2 | 10.2 |
| 3 | 10.4 |
| 4 | 10.8 |
| 5 | 12.8 |
| 6 | 13.8 |
| 7 | 14.2 |
| 8 | 14.8 |
| 9 | 15.0 |
| 10 | 16.4 |
| 11 | 16.8 |
| 12 | 17.8 |
| 13 | 18.0 |
| 14 | 18.6 |
| 15 | 19.0 |
| 16 | 19.4 |
| 17 | 19.8 |
| 18 | 20.2 |
| 19 | 20.6 |
| 20 | 21.2 |
| 21 | 21.4 |
| 22 | 23.0 |
| 23 | 23.4 |
| 24 | 24.6 |
| 25 | 26.0 |
| 26 | 28.0 |
| 27 | 29.0 |
| 28 | 30.4 |
| 29 | 31.0 |

The instant compound of formula I can also be obtained as in an amorphous modification having excellent solubility characteristics.

The instant invention also relates to a process for the preparation of this novel soluble crystalline modification of the compound of formula I which comprises dissolving the compound in an aromatic solvent and precipitating the compound by the addition of a lower alkanol; or by recrystallizing the compound from a lower alkanol alone in conjunction with a minor (up to 10% by volume) of toluene.

The instant invention also pertains to a composition stabilized against thermal, oxidative and actinic induced degradation which comprises (a) an organic material subject to thermal, oxidative or actinic induced degradation, and (b) an effective stabilizing amount (generally about 0.01 to about 5% by weight of the stabilized composition) of the soluble crystalline form of 2-(2-hydroxy-3-α-cumyl-5-tert-octylphenyl)-2H-benzotriazole, characterized by melting in the range of 109°–111° C. and by an X-ray diffraction pattern obtained using a Cu—Kα which exhibits diffraction angles (2Θ) as seen below:

| Peak No. | Diffraction Angle |
|---|---|
| 1 | 9.6 |
| 2 | 10.2 |
| 3 | 10.4 |
| 4 | 10.8 |
| 5 | 12.8 |
| 6 | 13.8 |
| 7 | 14.2 |
| 8 | 14.8 |
| 9 | 15.0 |
| 10 | 16.4 |
| 11 | 16.8 |
| 12 | 17.8 |
| 13 | 18.0 |
| 14 | 18.6 |
| 15 | 19.0 |
| 16 | 19.4 |
| 17 | 19.8 |
| 18 | 20.2 |
| 19 | 20.6 |
| 20 | 21.2 |
| 21 | 21.4 |
| 22 | 23.0 |
| 23 | 23.4 |
| 24 | 24.6 |
| 25 | 26.0 |
| 26 | 28.0 |
| 27 | 29.0 |
| 28 | 30.4 |
| 29 | 31.0 |

It is noted that the requirements for automotive paints and coatings have undergone a dramatic change in recent years. This coupled with increasing environmental concerns about the use of some aromatic hydrocarbon solvents has put great pressure on the industry to come up with new solutions to some very difficult challenges.

The benzotriazole UV absorbers have long been a mainstay in this area with 2-[2-hydroxy-3,5-di(α-cumyl)phenyl]-2H-benzotriazole being the workhorse and epitomy of what the benzotriazole UV absorbers can deliver. Unfortunately, this compound has only limited solubility (about 14% by weight) in toluene or xylene, and is sparingly soluble in environmentally more friendly solvents. This is becoming a severe limitation since the aromatic solvents are on their way out because of environmental concerns. Additionally, the relatively low solubility of said compound even in aromatic solvents limits the total concentration of benzotriazole UV absorber that can be added to the coating system. Since the life-time requirements for an automotive finish are doubling, the low solubility of said benzotriazole is a real hurdle.

Fortunately, there are soluble and thermally stable benzotriazole UV absorbers, chiefly the new soluble crystalline modification of 2-(2-hydroxy-3-α-cumyl-5-tert-octyl-phenyl)-2H-benzotriazole, which has the same low volatility and superior light stabilization effectiveness of 2-[2-hydroxy-3,5-di(α-cumyl)phenyl]-2H-benzotriazole, but which are soluble in environmentally friendly solvents and which can be added to the automotive finishes at a concentration sufficiently high to meet the new extended lifetime requirements for such finishes. This is demonstrated in the working Examples.

The instant compositions also pertain to a composition which additionally contains an effective stabilizing amount of a tris-aryl-s-triazine, a hindered amine light stabilizer or a mixture thereof.

Preferably such compositions contain additionally an effective stabilizing amount of 2,4-bis-(2,4-dimethylphenyl)-6-(2-hydroxy-4-octyloxyphenyl)-s-triazine;

2,4-bis-(2,4-dimethylphenyl)-6-(2-hydroxy-4-[3-(pentadecyloxy)-2-hydroxy-propoxy]-s-triazine;

bis-(1-octyloxy-2,2,6,6-tetramethylpiperidin-4-yl) sebacate;

bis-(1,2,2,6,6-pentamethylpiperidin-4-yl) sebacate;

N-1,2,2,6,6-pentamethylpiperidin-4-yl-n-dodecylsuccinimide; or

N-1-acetyl-2,2,6,6-tetramethylpiperidin-4-yl-n-dodecylsuccinimide.

The organic material (a) stabilized in such compositions is a polymeric film which is an acrylic/melamine resin, a polyester/melamine resin, an acrylic/urethane resin, a polyester/urethane resin, an epoxy/acid resin or a siloxane modified acrylic resin.

The instant invention also pertains to a polymer film composition which comprises (a) an electro coat primer in adhesion to a metal substrate; (b) a base or color coat that is in adhesion to the electrocoat and which comprises a film-forming binder and an organic pigment or an inorganic pigment or mixture thereof; (c) a clear coat that is in adhesion to the base coat and which comprises a film-forming binder; and (d) an effective stabilizing amount, between 1 and 20% by weight of the film-forming binder, of at least one soluble and thermally stable benzotriazole UV absorber contained in either the base coat or the clear coat or in both base coat and clear coat, preferably in the base coat.

The polymer film composition described above can also contain an additional layer between the electro coat primer and the base or color coat, which additional layer comprises (i) a film-forming binder and an organic pigment or an inorganic pigment or mixture thereof; and (ii) an effective stabilizing amount of at least one soluble and thermally stable benzotriazole UV absorber of formula I. Moreover, this additional layer can also contain an effective stabilizing mount of a hindered amine light stabilizer.

More particularly, the instant soluble and thermally stable benzotriazoles are of formula I

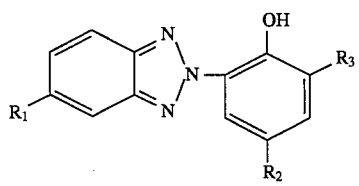

wherein

R₁ is hydrogen or chloro,

R₂ is alkyl of 4 to 28 carbon atoms or —$C_mH_{2m}COOR_4$ where m is 1 to 4 and R₄ is hydrogen or alkyl of 1 to 18 carbon atoms, and R₃ is α-cumyl.

Preferably, R₁ is hydrogen,

R₂ is alkyl of 8 to 12 carbon atoms or —$C_mH_{2m}COOR_4$ where m is or 4, and R₄ is alkyl of 8 to 12 carbon atoms, and R₃ is α-cumyl.

Most preferably, R₁ is hydrogen, R₂ is tert-octyl, nonyl or dodecyl, and R₃ is α-cumyl; and most especially where R₁ is hydrogen, R₂ is tert-octyl and R₃ is α-cumyl.

A preferred embodiment of the instant invention is to a composition stabilized against the deleterious effects of actinic light which comprises (a) an organic material subject to the deleterious effects of actinic light, and (b) an effective stabilizing amount of a soluble benzotriazole UV absorber which is 2-(2-hydroxy-3-α-cumyl-5-nonylphenyl)-2H-benzotriazole or 2-(2-hydroxy-3-α-cumyl-5-dodecylphenyl)-2H-benzotriazole.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

To attain maximum light stabilization, the concurrent use of other conventional light stabilizers can be advantageous. Examples of such stabilizers are UV absorbers of the benzophenone, benzotriazole, cyanoacrylate or oxanilide type, or metal-containing light stabilizers, for example, organic nickel compounds, or hindered amine light stabilizers. In two-coat systems, these additional light stabilizers can be added to the clear coat or both in the clear coat and in the pigments base coat.

The instant compositions also pertain to a composition which additionally contains an effective stabilizing mount of a tris-aryl-s-triazine, a hindered amine light stabilizer or a mixture thereof.

Preferably such compositions contain additionally an effective stabilizing amount of 2,4-bis-(2,4-dimethylphenyl)-6-(2-hydroxy-4-octyloxyphenyl)-s-triazine;

2,4-bis-(2,4-dimethylphenyl)-6-(2-hydroxy-4-[3-(pentadecyloxy)-2-hydroxy-propoxy]-s-triazine;

bis-(1-octyloxy-2,2,6,6-tetramethylpiperidin-4-yl) sebacate;

bis-(1,2,2,6,6-pentamethylpiperidin-4-yl) sebacate;

N-1,2,2,6,6-pentamethylpiperidin-4-yl-n-dodecylsuccinimide; or

N-1-acetyl-2,2,6,6-tetramethylpiperidin-4-yl-n-dodecylsuccinimide.

The organic material (a) stabilized in such compositions is a polymeric film which is an acrylic/melamine resin, a polyester/melamine resin, an acrylic/urethane resin, a polyester/urethane resin, an epoxy/acid resin or a siloxane modified acrylic resin.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(α-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer, and block polymers of styrene, such as, for example, styrene/butadiene/styrene,/isoprene/styrene, /ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on poly-butadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, poly-ethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxy-carboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed from about 1 to about 20% by weight of the stabilized composition, although this will vary with the particular substrate and application. An advantageous range is from 1 to 5%; preferably 1.5 to 2.5%.

The resulting stabilized compositions of the instant invention may optionally also contain from about 0.01 to about 5%, preferably from about 0.025 to about 2%, and especially from about 0.1 to about 1% by weight of various conventional additives, such as the materials listed below, or mixtures thereof.

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides.

Preferred UV absorbers are selected from the group consisting of 2-[2-hydroxy-3,5-di-($\alpha,\alpha$-dimethylbenzyl)phenyl]-2H-benzotriazole, 2-(2-hydroxy-3,5-di-tert-amylphenyl)-2H-benzotriazole, 2-[2-hydroxy-3-tert-butyl-5-($\omega$-hydroxy-octa(ethyleneoxy)carbonyl)ethylphenyl]-2H-benzotriazole, 2-[2-hydroxy-3-tert-butyl-5-(2- octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyl-oxy-5,5'-di-tert-butyloxanilide, 2-ethoxy-2'ethyloxanilide, 2,6-bis(2,4-dimethylphenyl)-4-(2-hydroxy-4-octyloxyphenyl-s-triazine, 2,6-bis(2,4-dimethylphenyl)-4-(2,4-dihydroxyphenyl)-s-triazine, 2,4-bis(2,4-dihydroxyphenyl)-6-(4-chlorophenyl)-, 2,6-bis(2,4-dimethylphenyl)-4-[2-hydroxy-4-(2-hydroxy-3-dodecyloxypropanoxy)-phenyl]-s-triazine and 2,2'-dihydroxy-4,4'-dimethoxybenzophenone.

Additional compositions of interest include those which additionally contain an effective stabilizing amount of a phenolic antioxidant; those which additionally contain a hindered amine derivative; or which additionally contain a phosphite or phosphonite stabilizer.

Compositions of special interest also include those wherein the organic material is an enamel of high solids content used for an industrial finish; is used as a coil coating; is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example.
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetra-methylbutyl)-phenol], such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octyl-amino-2,6-dichloro-s-triazine, tris-(2,2,6,6-tetramethylpiperidyl)-nitrilotriacetate, tetrakis-(2,2,6,6-tetramethyl-4-piperidyl)1,2,3,4-butanetetracarboxylate, 1,1'(1,2-ethanediyl)-bis-(3,3,5,5-tetramethylpiperazinone).

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyl-oxanilide and mixtures of ortho- and para-methoxy- as well as of o- and p-ethoxy-di-substituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-; 2,4-bis(2,4-dihydroxyphenyl)-6-(4-chlorophenyl)-; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy4-(2-hydroxyethoxy)phenyl]-6-(4-bromophenyl)-s-triazine; 2,4-bis[2-hydroxy-4-(2-acetoxy-ethoxy)phenyl]-6-(4-chlorophenyl)-s-triazine, 2,4-bis(2,4-dihydroxyphenyl)-6-(2,4-dimethylphenyl)-; 2,4-bis-(2,4-dimethylphenyl)-6-{2-hydroxy-4-[3-(2-ethylhexyl-oxy)-2-hydroxypropoxy]phenyl}-s-triazine; 2,4-bis-(2,4-dimethylphenyl)-6-{2-hydroxy-4-[3-(pentadecyloxy)-2-hydroxypropoxy]phenyl}-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxyl-amine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)-isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaocta-methylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octyl-thio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di-(3-tert-butyl-4-hydroxyphenyl)butyrate], octyl 3,5-di-tert-butyl-4-hydroxybenzylmercapto-acetate, bis(3,5-di-tert-butyl-4-hydroxyhydrocinnamoyl)hydrazide, and N,N'-bis-[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethyl-piperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl)1,2,3,4-butanetetracarboxylate, tetrakis(1,2,2,6,6-pentamethylpiperidin-4-yl)1,2,3,4-butanetetracarboxylate, polycondensation product of 2,4-dichloro-6-morpholino-s-triazine and 4,4'-hexamethylenebis(amino-2,2,6,6-tetramethylpiperidine),N,N',N'',N'''-tetrakis[(4,6-bis-butyl-2,2,6,6-tetramethyl-piperidin-4-yl)-amino-s-triazin-2-yl]-1,10-diamino-4,7-di-azadecane, mixed [2,2,6,6-tetramethylpiperidin-4-yl/β,β,β',β'-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl-n-dodecylsuccinimide, 1-acetyl-3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, 2,4-bis[N-(1-cyclohexyloxy-2,2,6,6-tetramethylpiperidin-4-yl)-n-butylamino]-6-[di-(2-hydroxyethyl)amino]-s-triazine, and 2,4-bis[N-(1-octyloxy-2,2,6,6-tetramethylpiperidin-4-yl)-n-butylamino]-6-[di-(2-hydroxyethyl)amino]-s-triazine.

A most preferred hindered amine compound is bis(2,2,6,6-tetramethyl-piperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, the polycondensation product of 1-(2-hydroxyethyl)-2,2,6,6-tetramethyl-4-hydroxy-piperidine and succinic acid, the polycondensation product of 2,4-dichloro-6-tert-octyl-amino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane, di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The process for the preparation of the soluble crystalline modification of the compound of formula I which is 2-(2-hydroxy-3-α-cumyl-5-tert-octylphenyl)-2H-benzotriazole comprises crystallizing or recrystallizing said compound of formula I from an alkanol of 1 to 4 carbon atoms either alone or in conjunction with a minor amount (up to 10% by volume) of toluene. Preferably the alkanol is an alkanol of 3 to 4 carbon atoms; most preferably isopropanol or 1-butanol.

Some alkanols useful in the instant process are, for example, methanol, ethanol, n-propanol, isopropanol, 1-butanol, sec-butyl alcohol or isobutyl alcohol.

Still another aspect of the instant invention is the application of the instant compounds of formula I in recording materials. The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example paper or plastic film, which has been coated with one or more layers. Depending on the type of the material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 (incorporated herein by reference).

The recording material can also be transparent, as, for example, in the case of projection films.

The compounds of the formula I can be incorporated into the carrier material as early as the production of the latter, in the production of paper, for example, by being added to the paper pulp. A second method of application is to spray the carrier material with an aqueous solution of compounds of the formula I or to add the compounds of the formula I to the coating composition.

Coating compositions intended for transparent recording materials suitable for projection cannot contain any particles which scatter light, such as pigments and fillers.

The dye-binding coating composition can contain a number of other additives, for example antioxidants, light stabilizers (including also UV absorbers which do not belong to the UV absorbers according to the invention), viscosity improvers, fluorescent brighteners, biocides and/or antistatic agents.

The coating composition is usually prepared as follows: the water-soluble components, for example the binder, are dissolved in water and stirred together. The solid components, for example fillers and other additives already described, are dispersed in this aqueous medium. Dispersion is advantageously carried out by means of devices, for example ultrasonic samples, turbine stirrers, homogenizers, colloid mills, bead mills, sand mills, high-speed stirrers and the like. It is a particular advantage of the compounds of the formula I that they can be incorporated easily into the coating composition.

The recording material according to this invention preferably contains 1 to 5000 mg/m$^2$, in particular 50–1200 mg/m$^2$, of a compound of the formula I.

As already mentioned, the recording materials according to the invention embrace a wide field. The compounds of the formula I can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,5365,463; 4,551,407; 4,562,137 and 4,608,330, also in EP-A 139,479; EP-A 162,664; EP-A 164,931; EP-A 237,024; EP-A 237,025 or EP-A 260,129. In all these systems the compounds of the formula I can be put into the dye-receiving layer. The compounds of the formula I can, however, also be put into the donor layer in order to protect the colour formers from light.

Photographic materials which can be stabilized are photographic dyes and layers containing such dyes or precursors thereof, for example photographic paper and films. Suitable materials are, for example, described in U.S. Pat. No. 5,364,749 (incorporated therein by reference). The compounds of the formula I act here as a UV filter against electrostatic flashes. In colour photographic materials couplers and dyes are also protected against photochemical decomposition.

The compounds of the formula I can be used for all types of colour photographic materials. For example, they can be employed for colour paper, colour reversal paper, direct-positive colour material, colour negative film, colour positive film, colour reversal film, etc. They are preferably used, inter alia, for photographic colour material which contains a reversal substrate or forms positives.

Colour-photographic recording materials usually contain, on a support, a blue-sensitive and/or a green-sensitive and/or a red-sensitive silver-halide emulsion layer and, if desired, a protection layer, the compounds of formula I being, preferably, either in the green-sensitive or the red-sensitive layer or in a layer between the green-sensitive and the red-sensitive layer or in a layer on top of the silver-halide emulsion layers.

The compounds of the formula I can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, they can be employed in recording materials for dye diffusion transfer printing, thermal wax transfer printing and dot matrix printing and for use with electrostatic, electrographic, electrophoretic, magnetographic and laser-electro-photographic printers and pen-plotters. Of the above, recording materials for dye diffusion transfer printing are preferred as, for example described in EP-A-507,734.

The compounds of the formula I can also be employed in inks, preferably for ink jet printing, as, for example, further described in U.S. Pat. No. 5,098,477 (incorporated herein by reference). A further subject of the present invention is, therefore, an ink containing at least one compound of the formula I as a stabilizer. The ink, particularly for ink jet printing, preferably contains water. Inks containing the stabilizer of the formula I in a concentration of 0.01 to 20% by weight, particularly 0.5 to 10% by weight, are also preferred.

X-ray diffraction patterns are recorded on a Philips Norelco X-ray Diffractometer unit, using Cu—Kα radiation with a nickel filter. All samples have a uniform particle size of 40 to 75 microns. This is the same particle size distribution obtained with the prior art compound of Example 2.

The following examples are presented for the purpose of illustration only and are not to be construed to limit the nature or scope of the instant invention in any manner whatsoever.

EXAMPLE 1

2-(2-hydroxy-3-α-cumyl-5-tert-octylphenyl)-2H-benzotriazole

The compound of formula I, 2-(2-hydroxy-3-α-cumyl-5-tert-octylphenyl)-2H-benzotriazole, is prepared according to the general procedure of Example 18 of U.S. Pat. No. 4,278,589. A 300 g sample of the compound of formula I is dissolved in 300 mL of xylene. To this solution is then added with stirring 600 mL of ethanol to afford 254 g of the novel soluble crystalline modification of the compound of formula I having a melting point of 109°–111° C.; and exhibiting only one spot in thin layer chromatography.

Analysis: Calcd for $C_{29}H_{35}N_3O$: C, 78.9; H, 8.0; N, 9.5. Found: C, 78.7; H, 8.1; N, 9.6.

This product has an X-ray diffraction pattern obtained using Cu—Kα which exhibits diffraction angles (2Θ) as seen below:

| Peak No. | Diffraction Angle |
| --- | --- |
| 1 | 9.6 |
| 2 | 10.2 |
| 3 | 10.4 |
| 4 | 10.8 |
| 5 | 12.8 |
| 6 | 13.8 |
| 7 | 14.2 |
| 8 | 14.8 |
| 9 | 15.0 |
| 10 | 16.4 |

-continued

| Peak No. | Diffraction Angle |
| --- | --- |
| 11 | 16.8 |
| 12 | 17.8 |
| 13 | 18.0 |
| 14 | 18.6 |
| 15 | 19.0 |
| 16 | 19.4 |
| 17 | 19.8 |
| 18 | 20.2 |
| 19 | 20.6 |
| 20 | 21.2 |
| 21 | 21.4 |
| 22 | 23.0 |
| 23 | 23.4 |
| 24 | 24.6 |
| 25 | 26.0 |
| 26 | 28.0 |
| 27 | 29.0 |
| 28 | 30.4 |
| 29 | 31.0 |

EXAMPLE 2

Comparative Example 2-(2-Hydroxy-3-α-cumyl-5-tert-octylphenyl)-2H-benzotriazole

The title compound is prepared as described in Example 18 of U.S. Pat. No. 4,278,589 as off-white crystals melting at 88°–90° C. This compound of formula I exhibits an X-ray diffraction pattern obtain using Cu—Kα which exhibits diffraction angles (2Θ) as seen below:

| Peak No. | Diffraction Angle |
| --- | --- |
| 1 | 5.2 |
| 2 | 6.2 |
| 3 | 6.8 |
| 4 | 9.2 |
| 5 | 9.7 |
| 6 | 11.0 |
| 7 | 12.0 |
| 8 | 12.2 |
| 9 | 13.0 |
| 10 | 13.6 |
| 11 | 14.6 |
| 12 | 15.4 |
| 13 | 15.6 |
| 14 | 16.4 |
| 15 | 17.8 |
| 16 | 18.8 |
| 17 | 19.4 |
| 18 | 19.8 |
| 19 | 20.4 |
| 20 | 21.0 |
| 21 | 22.4 |
| 22 | 22.8 |
| 23 | 23.4 |
| 24 | 24.2 |
| 25 | 25.0 |
| 26 | 25.4 |
| 27 | 26.0 |
| 28 | 27.6 |
| 29 | 29.4 |
| 30 | 30.8 |
| 31 | 31.2 |
| 32 | 32.4 |

A comparison of the X-ray diffraction patterns of the instant soluble crystalline modification as seen in Example 1 with the X-ray diffraction pattern of the prior art compound of Example 18 of U.S. Pat. No. 4,278,589 clearly indicates that the two materials are not the same.

EXAMPLE 3

Amorphous form of 2-(2-hydroxy-3-α-cumyl-5-tert-octylphenyl)-2H-benzotriazole

The compound prepared in Example 1 is heated to a melt and then allowed to resolidify. The amorphous material obtained has a melting point of 59°–74° C. Thin layer chromatography exhibits one spot identical to that obtained from the product of Example 1.

X-ray diffraction shows a featureless pattern confirming the amorphous nature of the compound obtained in this example.

EXAMPLE 4

2-(2-Hydroxy-3-α-cumyl-5-nonylphenyl)-2H-benzotriazole

The title compound is prepared according to the general procedure of Example 18 of U.S. Pat. No. 4,278,589 as an amber resin, but where the reduction of the corresponding o-nitroazobenzene intermediate is carried out using catalytic hydrogenation.

Analysis: Calcd for $C_{30}H_{37}N_3O$: C, 79.1; H, 8.2; N, 9.2. Found: C, 79.5; H, 8.5; N, 9.0.

EXAMPLE 5

5-Chloro-2-(2-hydroxy-3,5-di-tert-octylphenyl)-2H-benzotriazole

The title compound is prepared according to the general procedure of Example 18 of U.S. Pat. No. 4,278,589 as a pale yellow oil.

EXAMPLE 6

2-(2-Hydroxy-3-tert-octyl-5-α-cumylphenyl)-2H-benzotriazole

The title compound is prepared as described in Example 19 of U.S. Pat. No. 4,278,589.

EXAMPLE 7

2-(2-hydroxy-3-α-cumyl-5-tert-octylphenyl)-2H-benzotriazole

The title compound is prepared by the catalytic hydrogenation of the o-nitroazobenzene intermediate described in Example 17 of U.S. Pat. No. 4,278,589 as an off-white solid. A 100 g sample of said solid is recrystallized from 100 mL of isopropanol, again from 100 mL of 19:1 isopropanol:toluene and finally from 100 mL of 9:1 isopropanol:toluene to afford 78 g of the title compound melting at 109°–111° C. and having the same crystalline modification and X-ray diffraction pattern as the compound prepared in Example 1.

EXAMPLE 8

2-(2-Hydroxy-3-α-cumyl-5-nonylphenyl)-2H-benzotriazole

The title compound is prepared according to the general procedure of Example 18 of U.S. Pat. No. 4,278,589 as an amber resin.

EXAMPLE 9

2-(2-Hydroxy-3-α-cumyl-5-dodecylphenyl)-2H-benzotriazole

The title compound is prepared according to the general procedure of Example 18 of U.S. Pat. No. 4,278,589 as an amber resin.

EXAMPLE 10

2-(2-Hydroxy-3-α-cumyl-5-dodecylphenyl)-2H-benzotriazole

The title compound is prepared according to the general procedure of Example 18 of U.S. Pat. No. 4,278,589 as an amber resin, but where the reduction of the corresponding o-nitroazobenzene intermediate is carried out using catalytic hydrogenation.

EXAMPLES 11–12

Following the general procedure of Examples 1 and 7, the following compounds of formula I are prepared where $R_1$ is hydrogen and $R_3$ is α-cumyl.

| Example | $R_2$ |
| --- | --- |
| 11 | —$CH_2CH_2COOCH_3$ |
| 12 | —$CH_2CH_2COOC_8H_{17}$ |

EXAMPLE 13

Solubility in Organic Solvents

In order to incorporate a UV absorber stabilizer into the high solids thermoset acrylic resin systems, the UV absorber must be soluble in an appropriate organic solvent. To date solvents such as the aromatic hydrocarbons, toluene or xylene, have provided ample solubility for such UV absorbers, even the sparingly soluble 2-(2-hydroxy-3,5-di-α-cumylphenyl)-2H-benzotriazole.

However, the possible phasing out of such aromatic hydrocarbon solvents for environmental reasons, the trend to higher solids coatings, and the increasing demands of the automobile industry for automotive coatings that will last for up to 10 years means that a more soluble, non-volatile, but equally effective UV absorber will be required. Additionally, the UV absorber must be soluble in an environmentally friendly solvent.

The relative solubility of three different benzotriazole UV absorbers in a five typical organic solvents is measured by dissolving the benzotriazole UV absorber in 50–100 mL of five different solvents till the solutions become supersaturated. This is seen when the benzotriazole begins to settle to the bottom of the test flask. The supersaturated solutions are allowed to remain undisturbed overnight. Then, the top layer is decanted and filtered. The resulting filtrate containing the benzotriazole dissolved in the solvent is tested in triplicate for percent solids using ASTM Test Method D 2369-81. The higher the percent solids found indicates a more soluble benzotriazole. The results are seen in the table below.

Benzotriazole*
Solubility in grams/100 solvent

| Solvent** | UV Absorber | | | | |
| --- | --- | --- | --- | --- | --- |
| | A | B | C | D | E |
| xylene | 14 | 54 | 76 | >50 | >50 |
| butyl acetate | 6 | 27 | 33 | >50 | >50 |
| methyl amyl ketone | 4 | 24 | 33 | >50 | >50 |
| acetone | — | — | — | >50 | >50 |
| EXXATE ® 600 | 4 | 24 | 22 | >50 | >50 |
| PM acetate | 3 | 10 | 14 | >50 | >50 |
| PM solvent | — | 4 | 4 | — | — |

*A is 2-(2-hydroxy-3,5-di-α-cumylphenyl)-2H-benzotriazole.
B is 2-(2-hydroxy-3,5-di-tert-amylphenyl-2H-benzotriazole.
C is the compound of Example 7.
D is the compound of Example 4.
E is the compound of Example 10.
**EXXATE ® 600 is hexyl acetate from Exxon.
PM acetate is 1-methoxy-2-propyl acetate.
PM solvent is 1-methoxy-2-propanol Xylene is now a regulated solvent and is listed as a HAP's solvent (Hazardous Air Pollutant). As such, xylene is rapidly becoming phased out as a solvent for all types of coatings and an appropriate solvent substitute is becoming mandatory.

The other solvents listed in the table above are not currently targeted for regulation or removal and are becoming more common in the coatings industry.

The recent trend in the coatings industry is to higher solids coatings which means even less solvent to dissolve the UV absorber. The need for a more soluble, non-volatile UV absorber is most evident.

Inspection of the data in the table shows that UV absorber A is clearly less soluble in each of the solvents than is UV absorber B or C. In fact, the solubility of UN absorber A in any solvent other than xylene essentially removes it from consideration as a practical stabilizer in the new long term automotive coatings under the constraints listed above.

UV absorber B is clearly quite soluble even in the solvents other then xylene, but UV absorber B is too volatile for long term coating uses.

This leaves UV absorbers C–E which are even more soluble than UV absorber B, but also have the excellent non-volatility exhibited by UV absorber A. This combination of properties makes UV absorbers C–E prime candidates for use in long-term automotive high solids coatings.

EXAMPLE 14

The amorphous modification of 2-(2-hydroxy-3-α-cumyl-5-tert-octylphenyl)-2H-benzotriazole as prepared in Example 3 exhibits essentially the same solubility parameters in the various solvents as seen in Example 13 for the new crystalline modification of 2-(2-hydroxy-3-α-cumyl-5-tert-octylphenyl)-2H-benzotriazole prepared in Example 1 or 7 except that the amorphous form of 2-(2-hydroxy-3-α-cumyl-5-tert-octylphenyl)-2H-benzotriazole dissolves much more easily and rapidly in the non-HAPS solvents. This is a distinct advantage for using the amorphous compound of Example 3 in practical applications.

EXAMPLE 15

Gloss Retention of High Solids Thermoset Acrylic Clear Coats Containing UV Absorbers Applied Directly over a Silver Metallic Base Coat and a Electro Coat Primer Coated panels are prepared by spray applying a 1.8–2.0 mil (0.072–0.102 mm) thick film of a model HAPS-compliant high solids thermoset acrylic melamine clear coat containing 2% by weight of a test stabilizer over a commercially available silver metallic base coat, wet-on-wet, directly onto 4"×12" (10.16 cm×30.48 cm) UNIPRIME® panels obtained from Advanced Coating Technology, Inc. containing an electro coat primer. The coated panels are then baked at 250° F. (121° C.) for thirty minutes. The coated panels are then exposed in a Ci-65 Weather-O-meter (Arias Electric Devices) according to ASTM G 26–90. The gloss of the exposed panels is measured at 300 hour intervals. Higher gloss indicates greater protecting afforded to the coating by the soluble benzotriazole UV absorber.

The instant soluble compounds of formula I provide the coatings with good gloss retention.

Indeed, because a much higher concentration of soluble benzotriazole can be conveniently incorporated into the coating, the soluble benzotriazoles provide gloss retention for the high solids thermoset acrylic coating system far beyond that obtained where only a limited mount of benzotriazole is possible because of solubility limitations.

EXAMPLE 16

Gloss Retention of High Solids Thermoset Acrylic Clear Coats Containing UV Absorbers Applied Directly over a Silver Metallic Base Coat and a Electro Coat Primer Coated panels prepared as in Example 15 are also exposed in a QUV exposure device (Q Panel Co.) according to ASTM G 53. The 20° gloss is again measure at 300 hour intervals with higher gloss values indicating greater protection of the coating.

The instant soluble compounds of formula I provide the coatings with good gloss retention.

Indeed, because a much higher concentration of soluble benzotriazole can be conveniently incorporated into the coating, the soluble benzotriazoles provide gloss retention for the high solids thermoset acrylic coating system far beyond that obtained where only a limited amount of benzotriazole is possible because of solubility limitations.

Indeed, panels stabilized with a soluble benzotriazole UV absorber of formula I exhibit at least 50% gloss retention after 3000 hours in the QUV exposure device.

EXAMPLE 17

Gloss Retention of Acrylic Urethane Clear Coats Containing UV Absorbers Applied Directly over a Silver Metallic Base Coat and a Electro Coat Primer Coated panels are prepared by spray applying a 1.8–2.0 mil (0.036–0.051 mm) thick film of a model HAPS-compliant high solids acrylic urethane clear coat containing a test stabilizer over a commercially available silver metallic base coat, wet-on-wet, directly over 4"×12" (10.16 cm×30.48 cm) UNIPRIME® panels obtained from Advanced Coating Technology, Inc. containing an electro coat primer. The coated panels are then baked at 250° F. (121° C.) for thirty minutes. The coated panels are then exposed in a Ci-65 Weather-O-meter (Atlas Electric Devices) according to ASTM G 26-90. The gloss of the exposed panels is measured at 300 hour intervals. Higher gloss indicates greater protection afforded to the coating by the soluble benzotriazole UV absorber.

The instant soluble compounds of formula I provide the coatings with good gloss retention.

Indeed, because a much higher concentration of soluble benzotriazole can be conveniently incorporated into the coating, the soluble benzotriazoles provide gloss retention for the high solids thermoset acrylic coating system far beyond that obtained where only a limited amount of benzotriazole is possible because of solubility limitations.

EXAMPLE 18

Gloss Retention of Acrylic Urethane Clear Coats Containing UV Absorbers Applied Directly over a Silver Metallic Base Coat and a Electro Coat Primer Coated panels prepared as in Example 17 are also exposed in a QUV exposure device (Q Panel Co.) according to ASTM G 53. The 20° glass is again measure at 300 hour intervals with higher gloss values indicating greater protection of the coating.

The instant soluble compounds of formula I provide the coatings with good gloss retention.

Indeed, because a much higher concentration of soluble benzotriazole can be conveniently incorporated into the coating, the soluble benzotriazoles provide gloss retention for the high solids thermoset acrylic coating system far beyond that obtained where only a limited amount of benzotriazole is possible because of solubility limitations.

EXAMPLE 19

UVA Retention in High Solids Thermoset Acrylic Clear Coats Applied Directly over a Quartz Microscope Slide Coated quartz microscope slides are prepared by spray application of a 0.9–1.0 mil (0.018–0.026 mm) thick film of a model HAPS-compliant high solids thermoset acrylic melamine clear coat containing a test UV absorber. The coated quartz slides are then baked at 250° F. (121° C.) for 30 minutes. The optical density of the films is then measured at 345 nm.

The coated quartz slides are then exposed in a QUV exposure device (Q Panel Co.) according to ASTM G 53. The optical density is then measured again at 1000 hour intervals with higher optical density values indicating greater protection of the coating.

The instant soluble compounds of formula I provide the coatings with higher optical density values at all intervals.

Indeed, because a much higher concentration of soluble benzotriazole can be conveniently incorporated into the coating, the soluble benzotriazoles provide UVA retention for the high solids thermoset acrylic coating system far beyond that obtained where only a limited amount of benzotriazole is possible because of solubility limitations.

EXAMPLE 20

UVA Retention in High Solids Thermoset Acrylic Clear Coats Applied Directly over a Quartz Microscope Slide Coated quartz microscope slides are prepared according to the directions of Example 19. These coated slides are also exposed in a Ci-65 Weather-Ometer (Atlas Electric Devices) according to ASTM G-26-90. The optical density is measured at 1000 hour intervals with higher optical density values indicating greater protection of the coating.

The instant soluble compounds of formula I provide the coatings with higher optical density values at all intervals.

Indeed, because a much higher concentration of soluble benzotriazole can be conveniently incorporated into the coating, the soluble benzotriazoles provide UVA retention for the high solids thermoset acrylic coating system far beyond that obtained where only a limited amount of benzotriazole is possible because of solubility limitations.

EXAMPLE 21

The amount of UV absorber shown in the table below is dissolved in 2 ml of ethyl acetate. 1 ml of this solution is mixed with 9 ml of an aqueous gelatine solution [comprising 27.6 g/l of gelatine and 6.8 g/l of an 8% aqueous solution of 4,8-diisobutylnaphthalene-2-sulfonic acid (sodium salt) as wetting agent]. This mixture is emulsified for 3 minutes by means of ultrasound. 7.5 ml of this UV absorber emulsion are mixed with 4.5 ml of an aqueous curing agent solution (comprising 0.24% of 2-hydroxy-4,6-dichloro-s-triazine, potassium salt). 8 ml of this emulsion are poured onto a polyester base (13×18 cm). The casting is cured for 7 days at room temperature. A UV spectrometer is then used to determine the values for the maximum density in the range from 330–380 nm. The sample is then exposed in an Arias exposure unit with a total of 30, 60, 90 and 120 kJ/cm$^2$, the maximum density is remeasured, and the difference (–$\Delta D$ in %) between the corresponding values is calculated. The smaller is the $\Delta D$ value, the more stable is the UV absorber.

| Compound* | $D_{max}$ | mg/m$^2$ | $\Delta D$ in % | | | |
|---|---|---|---|---|---|---|
| | | | 30 KJ | 60 KJ | 90 KJ | 120 KJ |
| A | 2.0 | 492 | 4 | 8 | 16 | 25 |
| B | 2.1 | 640 | 5 | 10 | 17 | 25 |
| C | 2.1 | 560 | 4 | 7 | 12 | 24 |
| D | 1.9 | 560 | 0 | 5 | — | — |
| E | 2.0 | 660 | 3 | 4 | 5 | 7 |
| F | 1.9 | 726 | 2 | 4 | 5 | 8 |

*A is 2-(2-hydroxy-3-sec-butyl-5-tert-butylphenyl)-2H-benzotriazole.
B is 2-(2-hydroxy-3-dodecyl-5-methylphenyl)-2H-benzotriazole.
C is 2-(2-hydroxy-3,5-di-tert-amylphenyl)-2H-benzotriazole.
D is 2-(2-hydroxy-3,5-di-$\alpha$-cumylphenyl)-2H-benzotriazole.
E is 2-(2-hydroxy-3-$\alpha$-cumyl-5-tert-octylphenyl)-2H-benzotriazole.
F is 2-(2-hydroxy-3-$\alpha$-cumyl-5-dodecylphenyl)-2H-benzotriazole.

It is clear that the UV absorbers A, B and C which are not substituted with an $\alpha$-cumyl group at the 3-position of the 2-phenyl ring are not as photostable as the UV absorbers D, E and F which have such $\alpha$-cumyl substitution. UV absorber D with two $\alpha$-cumyl groups is no more stable than are UV absorbers E and F which have only one such $\alpha$-cumyl group in the 3-position, but which do not suffer from the solubility limitations of UV absorber D in non-HAPS solvents described earlier in this Specification.

What is claimed is:

1. A process for the preparation of the soluble crystalline form of the compound 2-(2-hydroxy-3-$\alpha$-cumyl-5-tert-octylphenyl)-2H-benzotriazole, characterized by melting in the range of 109°–111° C. and by an X-ray diffraction pattern obtained using Cu—K$\alpha$ which exhibits diffraction angles (2$\Theta$) as seen below:

| Peak No. | Diffraction Angle |
|---|---|
| 1 | 9.6 |
| 2 | 10.2 |
| 3 | 10.4 |
| 4 | 10.8 |
| 5 | 12.8 |
| 6 | 13.8 |
| 7 | 14.2 |
| 8 | 14.8 |
| 9 | 15.0 |
| 10 | 16.4 |
| 11 | 16.8 |
| 12 | 17.8 |
| 13 | 18.0 |
| 14 | 18.6 |
| 15 | 19.0 |
| 16 | 19.4 |
| 17 | 19.8 |
| 18 | 20.2 |
| 19 | 20.6 |
| 20 | 21.2 |
| 21 | 21.4 |
| 22 | 23.0 |
| 23 | 23.4 |
| 24 | 24.6 |
| 25 | 26.0 |
| 26 | 28.0 |
| 27 | 29.0 |
| 28 | 30.4 |
| 29 | 31.0 | which comprises
crystallizing or recrystallizing said compound from an alkanol of 1 to 4 carbon atoms either alone or in conjunction with a minor amount (up to 10% by volume) of toluene.

2. A process according to claim 1 wherein the alkanol is an alkanol of 2 to 4 carbon atoms.

3. A process according to claim 2 wherein the alkanol is isopropanol or 1-butanol.

4. The soluble crystalline form of 2-(2-hydroxy-3-$\alpha$-cumyl-5-tert-octylphenyl)-2H-benzotriazole, characterized by melting in the range of 109°–111° C. and by an X-ray diffraction pattern obtained using Cu—K$\alpha$ which exhibits diffraction angles (2$\Theta$) as seen below:

| Peak No. | Diffraction Angle |
|---|---|
| 1 | 9.6 |
| 2 | 10.2 |
| 3 | 10.4 |
| 4 | 10.8 |
| 5 | 12.8 |
| 6 | 13.8 |
| 7 | 14.2 |
| 8 | 14.8 |
| 9 | 15.0 |
| 10 | 16.4 |
| 11 | 16.8 |
| 12 | 17.8 |
| 13 | 18.0 |
| 14 | 18.6 |
| 15 | 19.0 |
| 16 | 19.4 |
| 17 | 19.8 |
| 18 | 20.2 |
| 19 | 20.6 |
| 20 | 21.2 |
| 21 | 21.4 |
| 22 | 23.0 |
| 23 | 23.4 |
| 24 | 24.6 |
| 25 | 26.0 |
| 26 | 28.0 |
| 27 | 29.0 |
| 28 | 30.4 |
| 29 | 31.0 |

5. Amorphous 2-(2-hydroxy-3-$\alpha$-cumyl-5-tert-octylphenyl)-2H-benzotriazole.

* * * * *